US012708472B2

(12) United States Patent
Sauter et al.

(10) Patent No.: US 12,708,472 B2
(45) Date of Patent: Aug. 18, 2026

(54) STERILE PACKAGING WITH INTEGRATED DAMPING

(71) Applicant: Aesculap AG, Tuttlingen (DE)

(72) Inventors: Wolfgang Sauter, Renquishausen (DE); Florian Etzel, Winnenden (DE)

(73) Assignee: Aesculap AG, Tuttlingen (DE)

( * ) Notice: Subject to any disclaimer, the term of this patent is extended or adjusted under 35 U.S.C. 154(b) by 0 days.

(21) Appl. No.: 18/856,155

(22) PCT Filed: Apr. 6, 2023

(86) PCT No.: PCT/EP2023/059276
§ 371 (c)(1),
(2) Date: Oct. 11, 2024

(87) PCT Pub. No.: WO2023/198633
PCT Pub. Date: Oct. 19, 2023

(65) Prior Publication Data

US 2025/0248780 A1 Aug. 7, 2025

(30) Foreign Application Priority Data

Apr. 12, 2022 (DE) ..................... 10 2022 108 827.8

(51) Int. Cl.
*A61B 50/30* (2016.01)
*A61B 50/00* (2016.01)

(52) U.S. Cl.
CPC ...... *A61B 50/30* (2016.02); *A61B 2050/0056* (2016.02); *A61B 2050/0066* (2016.02)

(58) Field of Classification Search
CPC .... B65D 81/052; B65D 81/07; B65D 81/075; B65D 5/5028; A61B 50/30
(Continued)

(56) References Cited

U.S. PATENT DOCUMENTS 5,272,856 A * 12/1993 Pharo .................. B65D 81/052 53/472
5,402,892 A 4/1995 Jaszai
(Continued)

FOREIGN PATENT DOCUMENTS

CN 105923271 A 9/2016
DE 19725499 A 12/1998
(Continued)

OTHER PUBLICATIONS

European Examination Report received in European Patent Application No. 23 716 616.0-1113 dated Nov. 26, 2024, with translation, 9 pages.

(Continued)

*Primary Examiner* — Steven A. Reynolds
(74) *Attorney, Agent, or Firm* — Christopher A. Rothe; CM Law

(57) ABSTRACT

A medicinal sterile packaging for packaging a medicinal product includes a first sterile barrier designed to receive the medicinal product in a heat-sealed/sealed manner. A second sterile barrier forms a receiving space for receiving the first sterile barrier in a heat-sealed/sealed manner. An outer protective packaging receives the first sterile barrier and the second sterile barrier. The second sterile barrier is a film that forms at least two air pockets separated from one another in the film by a predefined fold-over or folding edge. When the film is folded over along the fold-over or folding edge, the two air pockets come to lie one on top of the other in alignment, such that the receiving space can be produced between them.

17 Claims, 4 Drawing Sheets

(58) Field of Classification Search
USPC .......................................... 206/522, 438, 583
See application file for complete search history.

(56) References Cited

U.S. PATENT DOCUMENTS

| | | | | |
|---|---|---|---|---|
| 5,454,642 | A * | 10/1995 | De Luca | B65D 81/052 53/472 |
| 5,487,470 | A | 1/1996 | Pharo | |
| 5,620,096 | A * | 4/1997 | Pozzo | B65D 81/052 206/522 |
| 6,006,917 | A * | 12/1999 | Loeffler | B65D 5/5028 206/583 |
| 6,513,658 | B1 * | 2/2003 | Adkins | B65D 81/052 206/583 |
| 6,520,333 | B1 * | 2/2003 | Tschantz | B65D 81/052 383/3 |
| 8,047,378 | B2 * | 11/2011 | Eskenazi | B65D 43/162 206/594 |
| 8,963,345 | B2 * | 2/2015 | Cros | H10K 30/88 257/E23.116 |
| 11,897,682 | B2 * | 2/2024 | Borrero | B65D 81/052 |
| 2006/0042995 | A1 * | 3/2006 | McGrath | B65D 81/075 206/583 |
| 2008/0035519 | A1 * | 2/2008 | Swartz | B65D 81/03 206/522 |
| 2008/0260303 | A1 | 10/2008 | De Lesseux | |
| 2018/0222655 | A1 | 8/2018 | Grabowski | |
| 2019/0144190 | A1 | 5/2019 | Zhang | |

FOREIGN PATENT DOCUMENTS

| | | |
|---|---|---|
| JP | 2015-171909 A | 10/2015 |
| JP | 2016-179828 A | 10/2016 |
| WO | 90/09320 | 8/1990 |
| WO | 95/02548 | 1/1995 |
| WO | 98/51585 | 11/1998 |
| WO | 2006028933 A2 | 3/2006 |
| WO | 2018059468 A1 | 4/2018 |

OTHER PUBLICATIONS

Search Report received in German Patent Application No. DE 10 2022 108 827.8 dated Jan. 17, 2023, with translation, 9 pages.

International Search Report received in International Application No. PCT/EP2023/059276 dated Jun. 12, 2023, with translation, 6 pages.

* cited by examiner

S1
S2
S3
S4
S5
S6

STERILE PACKAGING WITH INTEGRATED DAMPING

CROSS-REFERENCE TO RELATED APPLICATIONS

This application is the United States entry of International Application No. PCT/EP2023/059276, filed on Apr. 6, 2023, and claims priority to German Application No. 10 2022 108 827.8, filed on Apr. 12, 2022. The contents of International Application No. PCT/EP2023/059276 and German Application No. 10 2022 108 827.8 are incorporated by reference herein in their entireties.

FIELD

The present disclosure relates to a sterile packaging of a medical product.

BACKGROUND

Medical products have to be packed in a suitable manner in order to maintain their sterility and to protect them from damage during their transportation and/or storage. In the recent past, sterile packaging with at least two sterile barriers, preferably made of a plastic material and/or a plastic film, as well as a further outer packaging, for example made of a cardboard material, have become established for this purpose.

It is known to store medical products such as implants, instruments, accessories, in particular tubes, containers, etc., syringes and similar medical utensils in sterile packaging that consists of an inner sterile barrier directly surrounding the medical product, an outer sterile barrier that supports the inner sterile barrier, and an outer packaging that houses the outer sterile barrier.

Often, at least one of the sterile barriers is additionally made of a puncture-resistant fabric to prevent the medical product from protruding outside. Sensor devices are also often provided within the respective sterile barriers, which indicate the penetration of air and thus indicate that the medical product contained therein is no longer sterile.

Generally, shock-absorbing packaging materials such as plastic films are also known to form bubble-like or tube-like compartments/pockets in which air is trapped, thus forming individual/separate air cushions evenly distributed over the plastic film. Their task is to protect the product packed in them against external influences such as vibrations or shocks. These can be generated, for example, by two plastic films laminated on top of each other, which form the self-contained air pockets at the appropriate place.

Alternatively, it is also known to provide outer packaging made of a multi-layer cardboard material with two parallel-spaced cover plates and a wave-shaped intermediate plate, which consequently deforms when an external force is applied and thus has a shock-absorbing effect.

Although the above packaging material can ensure both sterility and impact protection, problems have arisen in particular with regard to the latter property and in particular in the medical field, as indicated below:

With shock-absorbing cardboard boxes, it is necessary to store them in a dry place in order to maintain their shape, in particular the shape of the shock-absorbing intermediate layer. In addition, such materials are generally inelastic, i.e. they are plastically deformed by external forces and thus lose their original damping properties.

Shock-absorbing plastic films are generally ready-made products with standardized cushion pocket sizes and spacing. In unfavorable cases, products wrapped in them may therefore protrude in sections in areas between the cushioning pockets, thus forming unprotected, exposed product sections. Therefore, such products are often wrapped in several layers of such shock-absorbing plastic films in order to cushion any product sections that may protrude, although this makes the overall packaging layer considerably thicker.

SUMMARY

In view of the above-mentioned prior art, one object of the present disclosure is to provide a sterile medical packaging for medical products that provides suitable protection against external forces and ensures sufficient sterility of the product packaged therein.

The present disclosure thus relates to a sterile medical packaging for packaging a medical product, comprising a first sterile barrier prepared and configured to form a first receiving space for receiving the medical product in a preferably vacuumed, heat-sealed/sealed manner therein, a second sterile barrier prepared and configured to form a second receiving space for receiving the first sterile barrier, and an outer protective packaging prepared and configured to receive the first and second sterile barriers. According to the disclosure, the second sterile barrier comprises a film or a double membrane that forms at least two air pockets. The two air pockets are separated from each other by a predefined fold-down or folding edge, whereby, in the folded-down state of the double membrane or film along the fold-down or folding edge, the two air pockets come to lie in alignment with each other in such a way that the second receiving space can be created in between.

In other words, the present disclosure is that at least one of at least two sterile barriers comprises or is a film of the double membrane. One membrane of the film forms at least two air pockets bulging out on only one side of the film, whereas the other membrane remains essentially planar. The film furthermore has a predefined fold-down or folding edge that extends between the two air pockets in such a way that, in the folded-down state of the film along the predefined fold-down or folding edge, the air pockets come into essentially aligned contact and the planar membrane into essentially flat contact with each other in sections, so that the heat-sealable/sealable receiving space can be created between the planar membrane sections lying flat against each other in the area of the aligned air pockets, preferably by plastic or elastic deformation of the planar membrane sections lying flat against each other.

In yet other words, the sterile packaging comprises the first sterile barrier, the second sterile barrier and the outer protective packaging. The second sterile barrier is a two-layer film. Air is sealed in between the two films, causing the film to form air pockets. The air pockets of the film do not necessarily have to be configured symmetrically, but may have a bulged/concavely bulging side and a planar side. The air pockets are folded down around a folding edge so that the planar sides each abut against each other or are flush. The receiving space for receiving the first sterile barrier is configured between the planar sides/membrane sections.

The core of the present disclosure is therefore that the at least two air pockets are folded down around the first sterile barrier in such a way that the air pockets are each arranged one above the other and (completely) enclose/embrace the first sterile barrier, so as to (completely) accommodate the product to be stored between them. Accordingly, the receiving space for the first sterile barrier is formed at the contact surface of the two air pockets.

In this context, essentially planar means that the membrane is flat. However, pressure fluctuations in the air pocket, for example, may cause a slight convex bulge or an equally slight concave indentation in the elastic membrane. These slight deviations from the planar membrane are also to be regarded as essentially planar in the sense of the disclosure.

In particular, the fold-down or folding edge may form a fold line that separates two adjacent gas cushions, in particular air pockets/air cushions. In this case, the fold-down or folding edge in particular connects the two membranes of the double membrane. The fold-down or folding edge may be formed either by spot welding or by at least sectionally linear welding seams. If the fold-down or folding edge is realized by spot welding, then the adjacent air cushions can be connected to each other in sections in such a way that the air in the individual cushions can be connected. The weld seam may also extend over the entire length of the fold-down or folding edge, so that the individual air cushions are independent of each other. Furthermore, the linear weld seams may be interrupted and allow the individual air cushions to be connected to each other. Several weld seams or lines, for example two, may be arranged next to each other, in particular in parallel, and form the fold-down or folding edge between the air cushions.

The Present Disclosure has the Following Advantages:

Since the sterile packaging has two sterile barriers, the medical product in the sterile packaging is protected by double sterility.

The medical product is protected by the air pockets from external influences such as shocks or vibrations.

Since the air pockets are integrated into the sterile barrier, no additional air cushions or other cushioning means need to be incorporated into the outer protective packaging. This eliminates the need for parts and additional packaging steps.

Finally, the two air pockets form an intermediate gap in the folded state of the film, into which the product already shrink-wrapped in the first sterile barrier can be placed completely (with elastic deformation of the second sterile barrier), whereby it is completely surrounded by the (single-layer) air cushion. This ensures that the product is optimally protected while minimizing the amount of packaging material.

Preferably, the second sterile barrier has two air pockets, which are separated from each other by one or more predefined fold-down or folding edges and can be folded down in such a way that an additional pocket for receiving the first sterile barrier is positioned between the air pockets. The first sterile barrier with the medical product is introduced into the additional pocket of the second sterile barrier and is heat-sealed therein, preferably under vacuum. In addition to the additional pocket, the second sterile barrier may have the two air pockets, which are separated from the additional pocket by the at least one or more predefined fold-down or folding edges. This design is very easy to manufacture.

In other words, the second sterile barrier has two portions configured as air pockets and a portion configured as an additional receiving pocket, which are integrally joined together into a single component via fold-down or folding edges. The additional receiving pocket serves to receive the first sterile barrier and thus the medical product located therein. This virtually inevitably determines the relative position of the medical product to the two air pockets as soon as the medical product, together with the first sterile barrier surrounding it, is placed in the receiving pocket and, if applicable, fixed by vacuumizing the receiving pocket. If the air pockets are now folded over along the folded-over or folded edges, the medical product automatically comes to rest in the correct orientation between the air pockets.

In an advantageous configuration, the air pockets may be folded around the additional (receiving) pocket in such a way that the additional pocket is surrounded by the air pockets from at least two sides. The air pockets are at least partially compressible. This means that when the additional pocket with the first sterile barrier is placed with contact between the two air pockets, the air pockets are (partially) compressed and form the receiving space for the additional pocket and the medical product, including its first sterile barrier, in the additional pocket. As a result, the medical product is stored with cushioning and protected by the air pockets.

According to a further optional feature of the disclosure, the two air pockets are each arranged on opposite sides of the additional pocket. That is, an air pocket is arranged on each side of the additional pocket and is connected to the additional (receiving) pocket in each case via fold-down or folding edges in a single piece of material. The air pockets and the additional pocket are thus each spatially separated or spaced apart in a hinge-like manner by the fold-down or folding edges. In this configuration, each of the air pockets is folded around the fold-down or folding edges on an opposite side of the additional pocket (Z-shaped). The additional pocket is thus enclosed by the air pockets.

Alternatively, the two air pockets may be arranged on the same side of the additional pocket with the first sterile barrier. This means that on one side of the pocket, the air pockets are arranged next to each other. The air pockets are separated from each other by the fold-down or folding edges. The air pockets are also separated from the additional pocket by the fold-down or folding edge. When folding the air pockets around the additional pocket, the air pocket adjacent to the additional pocket is folded first. Then the additional air pocket is folded onto the side of the additional pocket that is opposite the first air pocket.

According to a further optional feature of the disclosure, the film of the second sterile barrier is made of a double membrane, wherein one membrane bulges outwards in a concave manner and one membrane remains planar. In other words, the film consists of two films. A first film forms the concave pockets, while a second film is planar and seals the pockets. The concave film side provides sufficient volume for the air within the air pockets. The planar membrane allows the planar membrane sections to lie against each other as flat as possible after folding over.

According to further optional feature of the disclosure, when the film is folded down, the planar membranes come to lie in sections against each other essentially flat. The planar membrane sections lying flat against each other form the receiving space for the first sterile barrier. As a result, the planar membrane sections enclose the first sterile barrier as completely as possible. The second sterile barrier is formed by enclosing the first sterile barrier with the membrane and then sealing the planar membrane sections.

According to a further optional feature of the disclosure, the heat-sealable/sealable receiving space is created between the planar membrane sections, which lie flat against each other, in the area of the aligned air pockets. The receiving space is preferably created by plastic or elastic deformation of the planar membrane sections which lie flat against each other. The elastic membrane deforms and takes on the shape of the first sterile barrier. Since the membrane takes on the shape of the first sterile barrier, the first sterile barrier is largely enclosed. This results in good cushioning with minimal movement and sterile packaging.

According to a further optional feature of the disclosure, the second sterile barrier is a film with a double membrane. A first convex membrane of the double membrane is made of a rigid material and a second, planar membrane is elastic. The first membrane is relatively firm so that it can be deep-drawn. The deep drawing forms the air pockets. Furthermore, the firm membrane acts as a puncture protection that prevents a pointed instrument from piercing through the sterile packaging. The second membrane is elastic so that it can take on the shape of the first sterile barrier and can largely enclose the first sterile barrier.

According to a further optional feature of the disclosure, the first sterile barrier comprises two films and is prepared and configured to heat-seal/seal the medical product between the two films such that relative movement between the films and the medical product is reduced. That is, the medical product is heat-sealed so tightly between the two films that it cannot move within the films. The reduced relative movement between the films and the medical product excludes or at least reduces the formation of particles due to friction between the films and the medical product. Particles can contaminate sterile medical products. In the worst case, this would result in repeated cleaning and sterilization. The tightly heat-sealed films thus provide a sterile barrier and also enable effective protection against particles and abrasion.

According to a further optional feature of the disclosure, the first sterile barrier is stored in a sterile manner in the second sterile barrier. In order to enable the functionality of a double sterile barrier or double sterility, the first sterile barrier has to be placed in an additional sterile packaging/second sterile barrier. This is the second sterile barrier. Since the second sterile barrier encompasses the first sterile barrier and is heat-sealed, it functions as a sterile barrier.

According to a further optional feature of the disclosure, the sterile packaging has several sealings. A first and a second sealing seal the first sterile barrier, a third, a fourth and a fifth sealing each seal the double membrane next to the air pockets of the second sterile barrier. A sixth sealing seals the two air pockets which lie on top of each other together.

The first sealing and the second sealing seal the two films of the first sterile packaging on both sides of the medical product. Three sealings hold the two membranes of the double membrane of the second sterile barrier together. The two membranes may also be two films that are heat-sealed together by the sealings. The three sealings are attached to the two outer sides of the air pockets and between the air pockets. The last sealing seals the two folded-down, abutting air pockets together to form the second sterile barrier around the first sterile barrier. The sealings ensure the sterility of the individual packaging layers or barriers.

According to a further optional feature of the disclosure, the second sterile barrier has exactly two air pockets. With two air pockets, exactly one medical product can be stored cushioned between the two air pockets. It is, of course, also conceivable that the second sterile barrier has several air pockets. This means that several medical products can be stored in a cushioned manner.

The object of the present disclosure can also be solved by a method for producing a sterile packaging according to one of the above aspects. The method according to the disclosure comprises the following steps: the first sterile barrier is produced by sealing two films (around the medical product). The second sterile barrier is produced, for example, by deep drawing and subsequent sealing of the air pockets. The first sterile barrier is placed on one of the planar membrane sections of the second sterile barrier or is inserted into a receiving pocket between the two air pockets, which are joined together with the two air pockets to form a single component and which are spatially separated from each other via fold lines. After placing/inserting the first sterile barrier, one of the air pockets is folded down in such a way that the air pockets enclose the first sterile barrier or the receiving pocket for the first sterile barrier. The planar membrane sections form the receiving space around the first sterile barrier/receiving pocket. The air pockets are sealed/heat-sealed in order to create the second sterile barrier around the first sterile barrier/receiving pocket. The second sterile barrier together with the first sterile barrier is placed in the outer protective packaging.

The method according to the disclosure has the following advantages. The cushioning for the first sterile barrier is integrated in the second sterile barrier. Thus, no additional air cushion film or similar cushioning means needs to be placed in the outer protective packaging. The method further provides a double sterile barrier very simply and at low cost.

It may also be advantageous to produce the second sterile barrier by heat-sealing the first sterile barrier in a sterile manner into the wider pocket of the second sterile barrier and then folding down the air pockets or air cushions of the second sterile barrier around the additional pocket. The air pockets and the sterile receiving pocket are therefore easy to produce.

The method may further include the following steps: the medical product is placed on a first film. A second film is placed on the first film with the medical product. After that, the two films are vacuum-sealed/heat-sealed on both sides of the medical product. Heat-sealing the medical product between the films creates a sterile barrier. The product cannot move or can only move minimally within the films. This prevents the abrasion of particles through friction.

Furthermore, the following steps may be carried out in the method according to the disclosure for producing the second sterile barrier:

- deep-drawing a first outer membrane in order to form the air pockets, which are adjacent to each other and open in the same direction;
- sealing the two adjacent air pockets at the respective openings via a second inner membrane in order to form adjacent air pockets with a curved and a planar side;
- after inserting the first sterile barrier, folding down the air pockets so that the air pockets are essentially aligned and the planar sides are flat against each other, forming a receiving space for receiving the first sterile barrier; and
- sealing the adjacent air pockets together.

The first membrane/film is deep-drawn in order to create open pockets/concave bulges. These open pockets are closed off by the second membrane/film. In order to do this, the two membranes are sealed together. The second sterile barrier now has the concavely bulging membrane and the planar membrane, which together form the air pockets. The first sterile barrier is placed on the planar membrane of the second sterile barrier. Then, one of the air pockets is folded down around the fold-down or folding edge. The air pockets are folded down in such a way that the air pockets are essentially aligned and the planar sides are flat against each other. The planar sides form the receiving space for the first sterile barrier. In order to do this, the elastic, planar membrane sections adapt to the shape of the first sterile barrier.

The process provides the second sterile barrier with integrated air pockets in a simple and cost-effective way.

The present disclosure further relates to a system comprising a medical sterile packaging according to one of the preceding aspects and a medical product that is packaged in a sterile manner in the medical sterile packaging. The at least two air pockets of the second sterile barrier are folded down around the medical product such that a planar membrane of the second sterile barrier faces toward the medical product and the receiving space for receiving the first sterile barrier is configured in the planar membrane. The elastic, planar membrane takes on the shape of the first sterile barrier and completely covers the first sterile barrier. This ensures that the first sterile barrier cannot move within the second sterile barrier and is also stored in a sterile manner in the second sterile barrier. The other convex membrane is rigid and cannot adapt to the shape of the first sterile barrier.

According to further optional feature of the disclosure, the extent of the planar membrane is greater than that of the medical product. The receiving space of the planar membrane completely or almost completely encloses the medical product. Since the planar membrane section that covers the first sterile barrier is larger than the medical product and thus also larger than the first sterile barrier with the medical product, the planar membrane section can completely cover the first sterile barrier.

DETAILED DESCRIPTION

Figure 1:
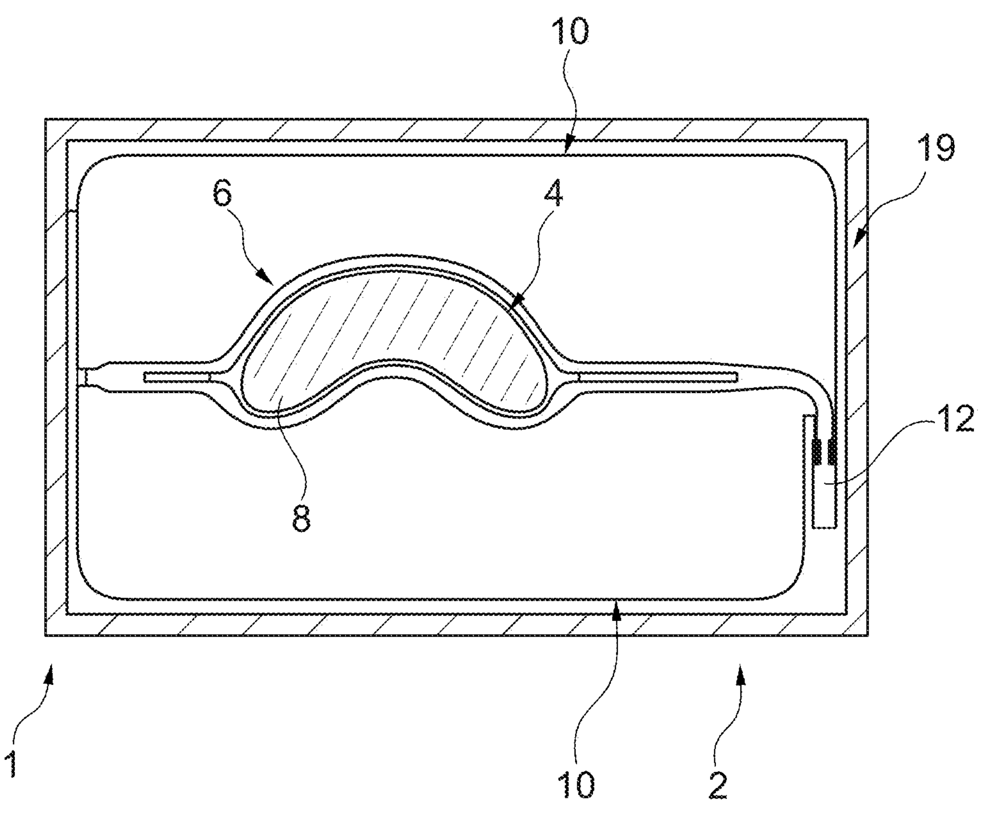
FIG. 1 shows a longitudinal section through a sterile packaging according to a first embodiment of the present disclosure with a first sterile barrier and a second sterile barrier.

FIG. 1 shows a longitudinal section through a sterile packaging 1. The sterile packaging 1 comprises a protective packaging 2, which is preferably a cardboard box. The protective packaging 2 is approximately rectangular. Two sterile barriers are arranged within the protective packaging 2. A first sterile barrier 4 is arranged in a sterile manner within a second sterile barrier 6. A medical product 8 is sealed or heat-sealed inside the first sterile barrier 4. The second sterile barrier 6 surrounds the first sterile barrier 4 and is in contact on its outer side with the protective packaging 2. I.e. the first sterile barrier 4 is completely enclosed by the second sterile barrier 6. The second sterile barrier 6 has two elongated air pockets 10. One of the two air pockets 10 in each case almost fills half of the volume of the protective packaging 2. Thus, the two air pockets 10 divide the protective packaging 2 into two halves. The first sterile barrier 4 is supported between the two air pockets 10. The two air pockets 10 are connected by heat-sealing on one side. On the other side, the two air pockets 10 each have a heat-sealed corner 12. The two heat-sealed corners 12 are connected by heat-sealing. Thus, the two air pockets 10 completely surround the first sterile barrier 4.

The two air pockets 10 support the first sterile barrier 4 in a cushioning manner. This means that the two air pockets 10 protect the sterile barrier 4 from vibrations. In addition, the two air pockets 10 stabilize the protective packaging 2. Due to the sealed heat-sealed corner 12, the first sterile barrier 4 is stored in a sterile manner within the second sterile barrier 6.

Figure 2:
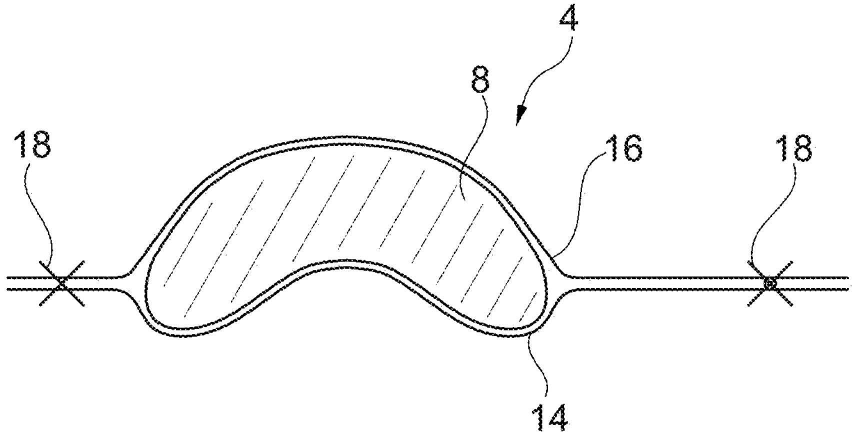
FIG. 2 shows a longitudinal section through the first sterile barrier with a medical device.

FIG. 2 shows a longitudinal section through the first sterile barrier 4. The first sterile barrier 4 comprises two films, namely a lower film 14 and an upper film 16. The medical product 8 lies on the lower film 14. The upper film 16 is placed on the lower film 14 with the medical product 8 and vacuumized with the lower film connected by heat-sealing. The lower film 14 and the upper film 16 are thereby connected by heat-sealing on both sides of the medical product 8. This results in two sealings 18.

Due to the vacuum sealing of the medical product 8 in the lower film 14 and the upper film 16, there is no or only minimal relative movement between the medical product 8 and the two films 14, 16, even when the sterile packaging 1 is subject to heavy transport loads. This helps to prevent or at least reduce the formation of particles through abrasion. The first sterile barrier 4 thus provides simultaneous protection against particles and abrasion.

Figures 3, 4:
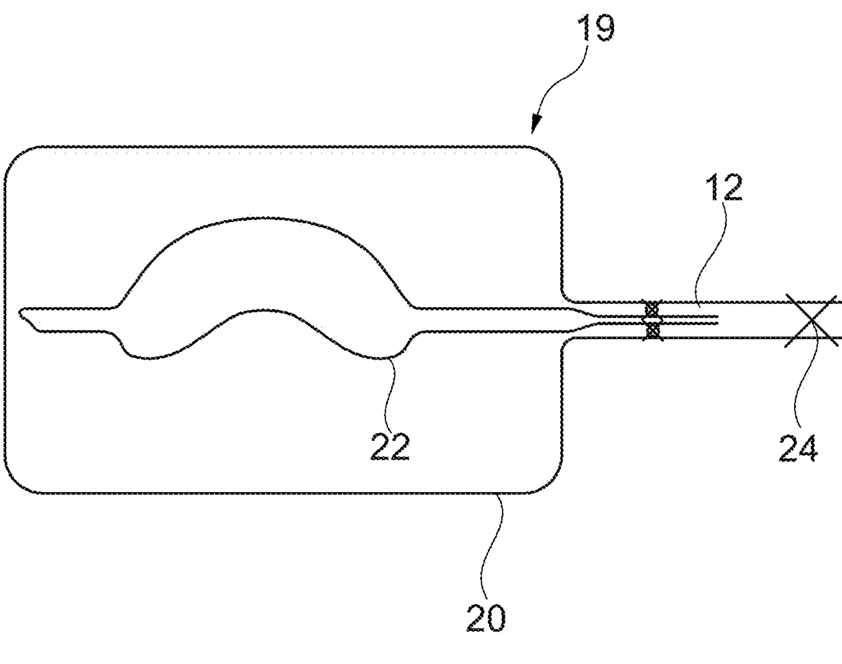
FIG. 3 shows a longitudinal section through the second sterile barrier.
FIG. 4 shows a flow chart of a method for producing the sterile packaging according to the disclosure.

FIG. 3 shows a longitudinal section through the second sterile barrier 6. The first sterile barrier 4 is embedded between the two air pockets 10 of the second sterile barrier 6. The second sterile barrier 6 is or consists of a film that is a double membrane 19. The double membrane 19 has a first (outer) membrane 20 and a second (inner) membrane 22. The (outer) membrane 20 is in contact with the protective packaging 2 and is rigid. That is, the (outer) membrane 20 is not elastic or not readily deformable. The (inner) membrane 22 is in contact with the first sterile barrier 4 and is elastic. This means that the first sterile barrier 4 sinks into the (inner) membrane 22, the membrane 22 adapts to the shape of the first sterile barrier 4 and encloses it (almost) completely. The (inner) membrane 22 forms a receiving space 23 for the first sterile barrier 4. The two air pockets 10 are each hermetically sealed. The two heat-sealed corners 12 of the two air pockets 10 are heat-sealed/sealed to each other and thus form a common heat-sealed corner of the second sterile barrier 6. The two heat-sealed corners 12 are heat-sealed/sealed to each other with a seal 24.

FIG. 4 shows a flow chart of a process for manufacturing the sterile packaging 1. In a first step S1, the first sterile barrier 4 is produced by sealing the medical product 8 between two films 14, 16. In this process, the medical product 8 is placed on the lower film 14, covered with the upper film 16 and the two films 14, 16 are heat-sealed under vacuum. In a further step S2, two pockets 26 are formed in the rigid (outer) membrane 20 of the second sterile barrier 6 by deep-drawing. The pockets 26 are adjacent to each other and both open in the same direction. The two adjacent pockets 26 are hermetically sealed with the elastic (inner) membrane 22. The elastic (inner) membrane 22 is sealed by three sealings 28, once outside the pockets 26 and once between the pockets 26. By sealing the two membranes 20, 22, the two air pockets 10 are configured with the heat-sealed corners 12. A fold-down or folding edge 30 is positioned between the adjacent air pockets 10. In a further step S3, the first sterile barrier 4 is placed on the elastic (inner) membrane 22 of one of the air pockets 10. The elastic (inner) membrane 22 yields and adapts to the shape of the first sterile barrier 4. The air pocket 10 on which the first sterile barrier 4 is not located is folded down in a further step S4 around the fold-down or folding edge 30, wherein the sealing between the two air pockets 10 is the fold-down or folding edge 30. One of the air pockets 10 is folded down in such a way that an upper air pocket rests on the lower air pocket, the elastic (inner) membrane sections of the air pockets 10 touch and surround the first sterile barrier 4. The elastic (inner) membrane 22 forms the receiving space 23 for the first sterile barrier 4. The two heat-sealed corners 12 are heat-sealed/sealed to each other in step S5. The folded-down and sealed second sterile barrier 6 together with the first sterile barrier 4 is placed in the protective packaging 2 in a final step S6 and the protective packaging 2 is sealed.

Figure 5:
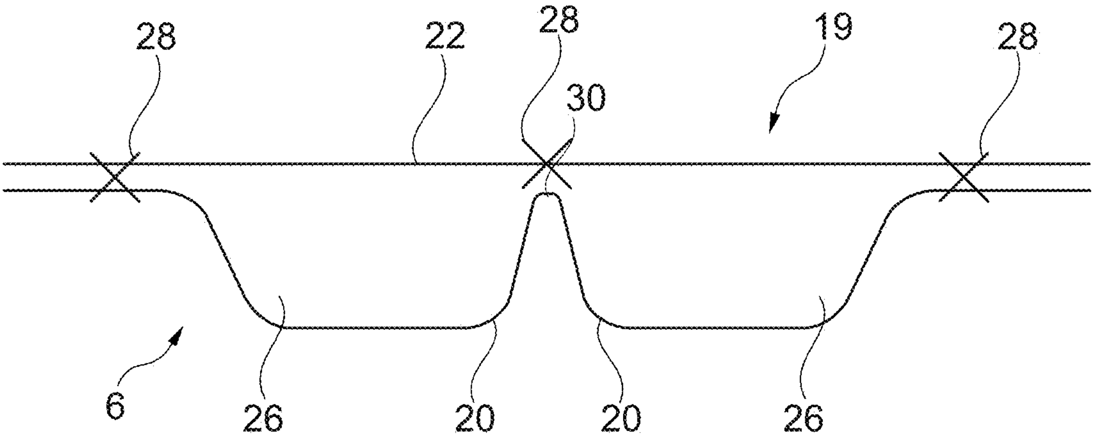
FIG. 5 shows the second sterile barrier during manufacture according to the method according to the disclosure.

FIG. 5 shows the double membrane 19 of the second sterile barrier 6 after step S2. The two pockets 26 of the lower film 20 are configured. The elastic (inner) membrane 22 is heat-sealed onto the openings of the pockets 26 to form the air pockets 10. The three weld spots/sealings 28 are configured for this purpose. The fold-down or folding edge 30 is configured between the two pockets 26.

Figure 6:
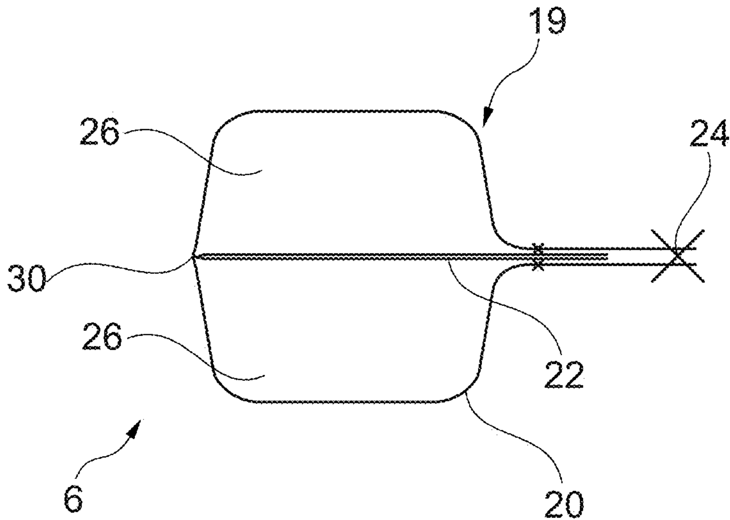
FIG. 6 shows the second sterile barrier in the finished state.

FIG. 6 shows the double membrane 19 of the second sterile barrier 6 after manufacturing. In this case, the two pockets 26 are folded onto each other and the two heat-sealed corners 12 are heat-sealed to each other. The second sterile barrier 6 therefore has the weld point/seal 24.

Figure 7:
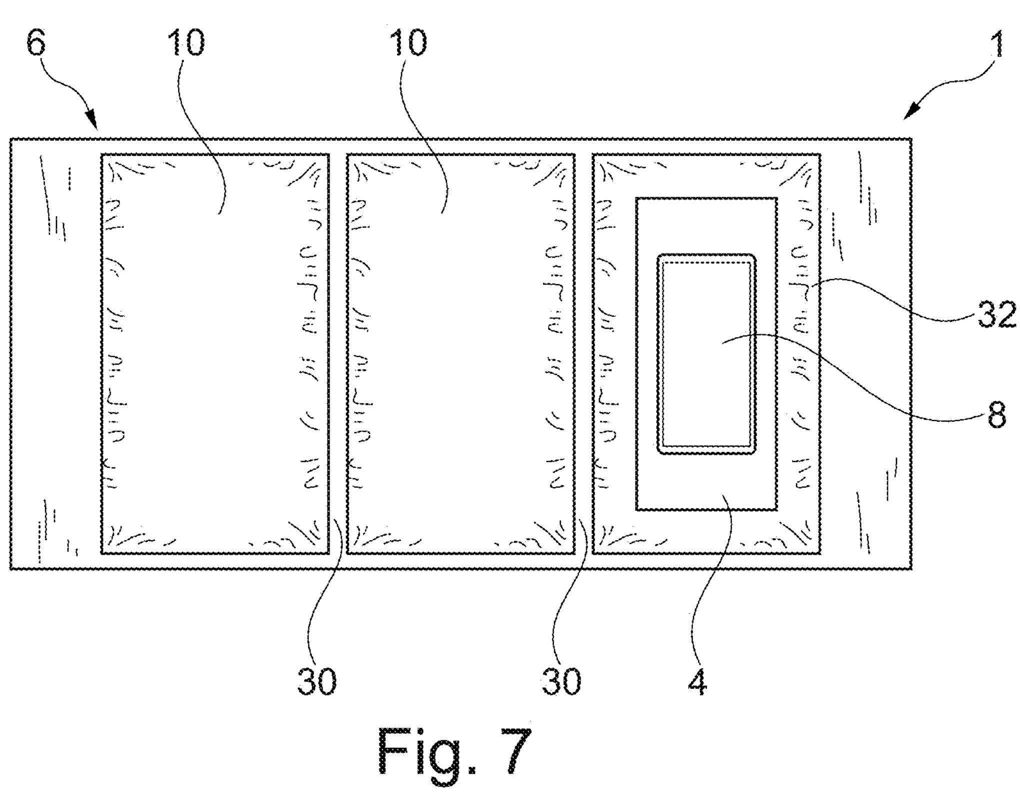
FIG. 7 shows a sterile packaging according to a second embodiment of the present disclosure.

FIG. 7 shows a sterile packaging 1 according to a second embodiment in an unfolded state. The sterile packaging 1 is therefore an integral component consisting of the second sterile barrier 6 with the two (elongated/rectangular) air pockets 10 and an additional receiving pocket 32 for receiving a medical product, which in turn is packed in the first sterile barrier. In this example, the two air pockets 10 are positioned directly next to each other and separated from each other by the (one) fold-down or folding edge 30. The second sterile barrier 6 has the additional pocket 32, which is prepared and configured to receive the first sterile barrier 4 and thus the product packaged therein. The additional pocket 32 is separated from the one air pocket 10 by an additional fold-down or folding edge 30, which is positioned directly next to the pocket 32. The medical product 8 is placed in the pocket 32 and is preferably vacuumed and heat-sealed/sealed in this pocket. The air pockets are (continuously) folded/wrapped around the pocket 32 with the first sterile barrier 4 in such a way that an air pocket 10 rests against each side of the pocket 32. The air pockets 10 are partially compressible and form between them the receiving space 23 for the pocket 32 with the first sterile barrier 4. The fold-down or folding edges 30, which separate the two air pockets 10 and the additional pocket 32, may be configured as a linear and/or point-shaped weld seam. The linear weld seam may extend over the entire length of the edge, but it may also be interrupted. If the weld seam is interrupted in a linear or point-shaped manner, the air pockets may be in (fluid) communication with each other. The fold-down or folding edges 30 may also consist of several parallel weld seams.

The air pocket 10, which is positioned directly next to the pocket 32, is first folded down onto one side of the pocket 32. The other air pocket 10 is then folded down again to rest on the opposite side of the pocket 32. As a result, the pocket 32 is surrounded and protected by the air pockets on both sides.

Figure 8:
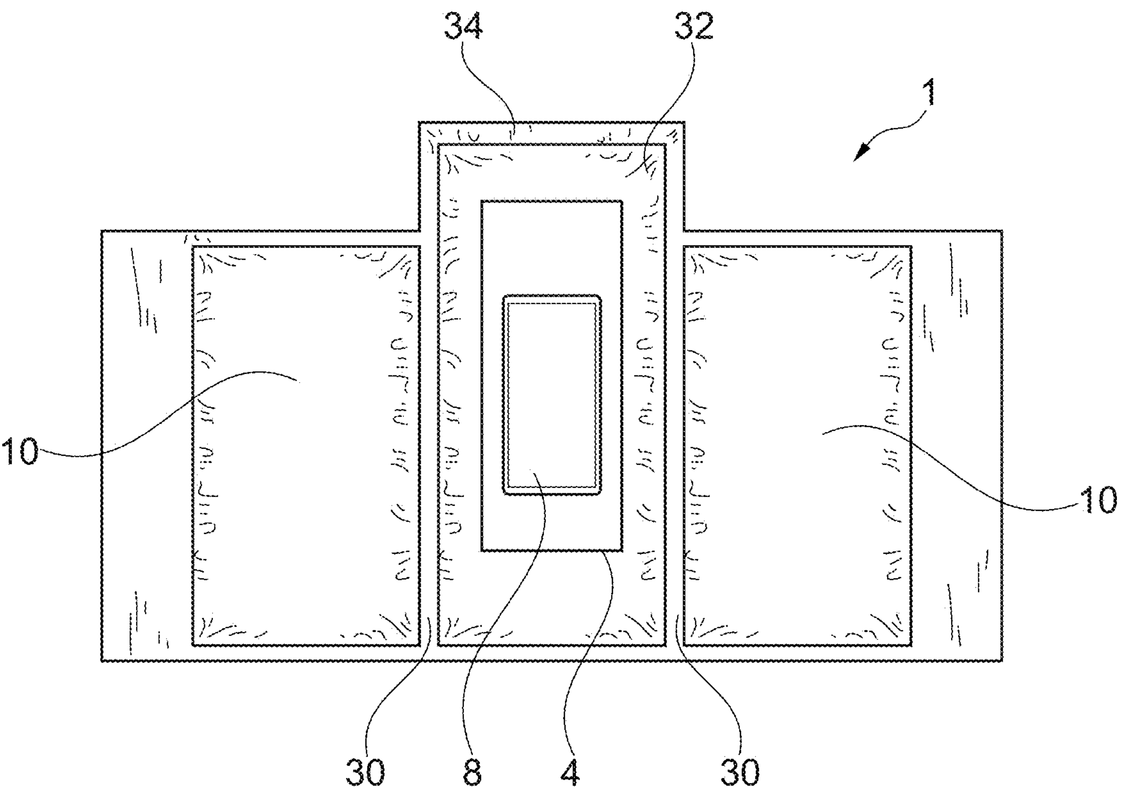
FIG. 8 shows a sterile packaging according to a third embodiment of the present disclosure.

FIG. 8 shows a sterile packaging 1 according to a third embodiment in an unfolded state. In this embodiment, the two air pockets 10 are positioned on two opposite sides of the pocket 32 with the first sterile barrier 4 located therein. The pocket 32 is therefore arranged between the two air pockets 10. The pocket 32 is separated from the air pockets by the fold-down or folding edge 30. The pocket 32 has a tab 34 for sealing the pocket 32 after the first sterile barrier 4 with the medical product 8 has been inserted. The two air pockets are each folded down at the fold-down or folding edge 30 so that one air pocket rests against each side of the pocket 32. As a result, the pocket and the medical product 8 in the pocket are located in the receiving space 23 between the air pockets 10 and are protected from (at least) two sides.

LIST OF REFERENCE SIGNS

1 sterile packaging
2 outer protective packaging
4 first sterile barrier
6 second sterile barrier
8 medical product
10 air pocket
18 sealing
19 double membrane
20 (outer) membrane
22 (inner) membrane
23 receiving space
24 sealing
28 sealing
30 fold-down or folding edge
32 additional pocket
34 tab

The invention claimed is:

1. A sterile medical packaging for packaging a medical product, the sterile medical packaging comprising:
- a first sterile barrier;
- a second sterile barrier; and
- an outer protective packaging,
- the first sterile barrier configured to receive the medical product in a sealed manner,
- the second sterile barrier configured to form a receiving space for receiving the first sterile barrier in a sealed manner,
- the outer protective packaging configured to receive the first sterile barrier and the second sterile barrier,
- the second sterile barrier consisting of a double membrane forming exactly two air pockets,
- the exactly two air pockets being separated from each other by a predefined folding edge in the double membrane,
- the double membrane being foldable into a folded-down state along the predefined folding edge, and
- the exactly two air pockets being aligned with each other in the folded-down state such that the receiving space is created between the exactly two air pockets.

2. The sterile medical packaging according to claim 1, wherein:
- the double membrane comprises an inner membrane and an outer membrane,
- the outer membrane bulges out concavely, and
- the inner membrane is planar.

3. The sterile medical packaging according to claim 2, wherein the predefined folding edge connects the inner membrane and the outer membrane.

4. The sterile medical packaging according to claim 3, wherein the predefined folding edge comprises a point-shaped or line-shaped weld seam.

5. The sterile medical packaging according to claim 2, wherein the outer membrane is made of a rigid material and the inner membrane is elastic.

6. The sterile medical packaging according to claim 2, wherein:

the inner membrane comprises at least two inner membrane sections, the at least two inner membrane sections are aligned adjacent to each other in proximity to the exactly two air pockets in the folded-down state, and the receiving space is positioned between the at least two inner membrane sections.

7. The sterile medical packaging according to claim 6, wherein the receiving space is formable by plastic or elastic deformation of the at least two inner membrane sections.

8. The sterile medical packaging according to claim 6, wherein the at least two inner membrane sections lie flat in sections against each other in the folded-down state.

9. The sterile medical packaging according to claim 1, wherein:

the first sterile barrier comprises two films, and the first sterile barrier is configured to seal the medical product between the two films to limit movement of the medical product relative to the two films.

10. The sterile medical packaging according to claim 1, wherein:

the sterile medical packaging comprises a first sealing, a second sealing, a third sealing, a fourth sealing, a fifth sealing, and a sixth sealing, the first sealing and the second sealing seal the first sterile barrier, the third sealing, the fourth sealing and the fifth sealing each seal the double membrane next to the exactly two air pockets, and the sixth sealing seals the exactly two air pockets.

11. A system comprising:

the sterile medical packaging according to claim 1; and a medical product that is packaged in a sterile manner in the sterile medical packaging, the exactly two air pockets being folded down around the medical product such that a planar membrane of the double membrane faces toward the medical product and the receiving space is configured in the planar membrane.

12. The system according to claim 11, wherein the planar membrane extends beyond the medical product, and the receiving space completely encloses the medical product.

13. A sterile medical packaging for packaging a medical product, the sterile medical packaging comprising:

a first sterile barrier configured to receive the medical product in a sealed manner;

a second sterile barrier extending from a first side edge to a second side edge and comprising an inner membrane and an outer membrane, wherein the inner membrane and the outer membrane are secured together to define:

a first region adjacent to the first side edge and having a first pocket between the outer membrane and the inner membrane, a second region secured to the first region by a first folding edge where the inner membrane is secured to the outer membrane by a first weld seam, the second region having a second pocket between the outer membrane and the inner membrane, and a third region adjacent to the second side edge and secured to the second region by a second folding edge where the inner membrane is secured to the outer membrane by a second weld seam, the third region having a third pocket between the outer membrane and the inner membrane, wherein one of the first pocket, the second pocket and the third pocket is configured to receive the first sterile barrier in a sealed manner, wherein the first region, the second region and the third region are movable from a flat state in which the first region, the second region and the third region are aligned in a row along a plane with the first folding edge and the second folding edge located between the first side edge and the second side edge, and a folded state in which the first region, the second region and the third region are stacked in a direction perpendicular to the plane; and an outer protective packaging configured to receive the first sterile barrier and the second sterile barrier.

14. The sterile medical packaging according to claim 13, wherein the first pocket and the second pocket are each arranged on opposite sides of the third pocket, and the first sterile barrier is located in the third pocket.

15. The sterile medical packaging according to claim 13, wherein the third pocket is configured to receive the first sterile barrier.

16. The sterile medical packaging according to claim 13, wherein the first region and the second region are folded down the first folding edge and the second folding edge in such a way that the third pocket is surrounded, perpendicular to the plane, by the first pocket and the second pocket.

17. The sterile medical packaging according to claim 13, wherein the third pocket is configured to receive the first sterile barrier and the first weld seam is interrupted such that the first pocket is in fluid communication with the second pocket.

* * * * *